(12) United States Patent
Chen

(10) Patent No.: US 8,313,225 B1
(45) Date of Patent: Nov. 20, 2012

(54) ELECTRONIC INCENSE ASSEMBLY

(75) Inventor: Po-Chou Chen, New Taipei (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 0 days.

(21) Appl. No.: 13/456,247

(22) Filed: Apr. 26, 2012

(30) Foreign Application Priority Data

Dec. 23, 2011 (TW) .............................. 100148203 A

(51) Int. Cl.
*G02B 6/00* (2006.01)
(52) U.S. Cl. .................... 362/565; 362/554; 362/559
(58) Field of Classification Search .................. 422/120, 422/126; 362/551, 554, 559, 565
See application file for complete search history.

(56) References Cited

U.S. PATENT DOCUMENTS 7,575,356 B1 * 8/2009 Bouchard .................... 362/571

FOREIGN PATENT DOCUMENTS

JP 2004-275393 * 10/2004

OTHER PUBLICATIONS

English Language Derwent abstract for JP 2004-275393; published Oct. 2004.*

* cited by examiner

*Primary Examiner* — Sean E Conley
(74) *Attorney, Agent, or Firm* — Altis Law Group, Inc.

(57) ABSTRACT

An electronic incense assembly includes a number of electronic incense sticks, a light source, a converging lens, a fiber optic coupler, and a number of fibers. Each of the electronic incense sticks includes a transparent tube having a first end and a second end, a bubble forming at the first end, an opaque coating on the outer surface of a part of the tube adjacent to the first end. The light source is for emitting light. The converging lens is for converging the light. The fiber optic coupler includes an input for receiving the converged light and a plurality of outputs and is configured for transmitting the converged light entering the input to the outputs. The fibers connect to the outputs respectively and extend through the tubes to the bubbles respectively.

1 Claim, 1 Drawing Sheet

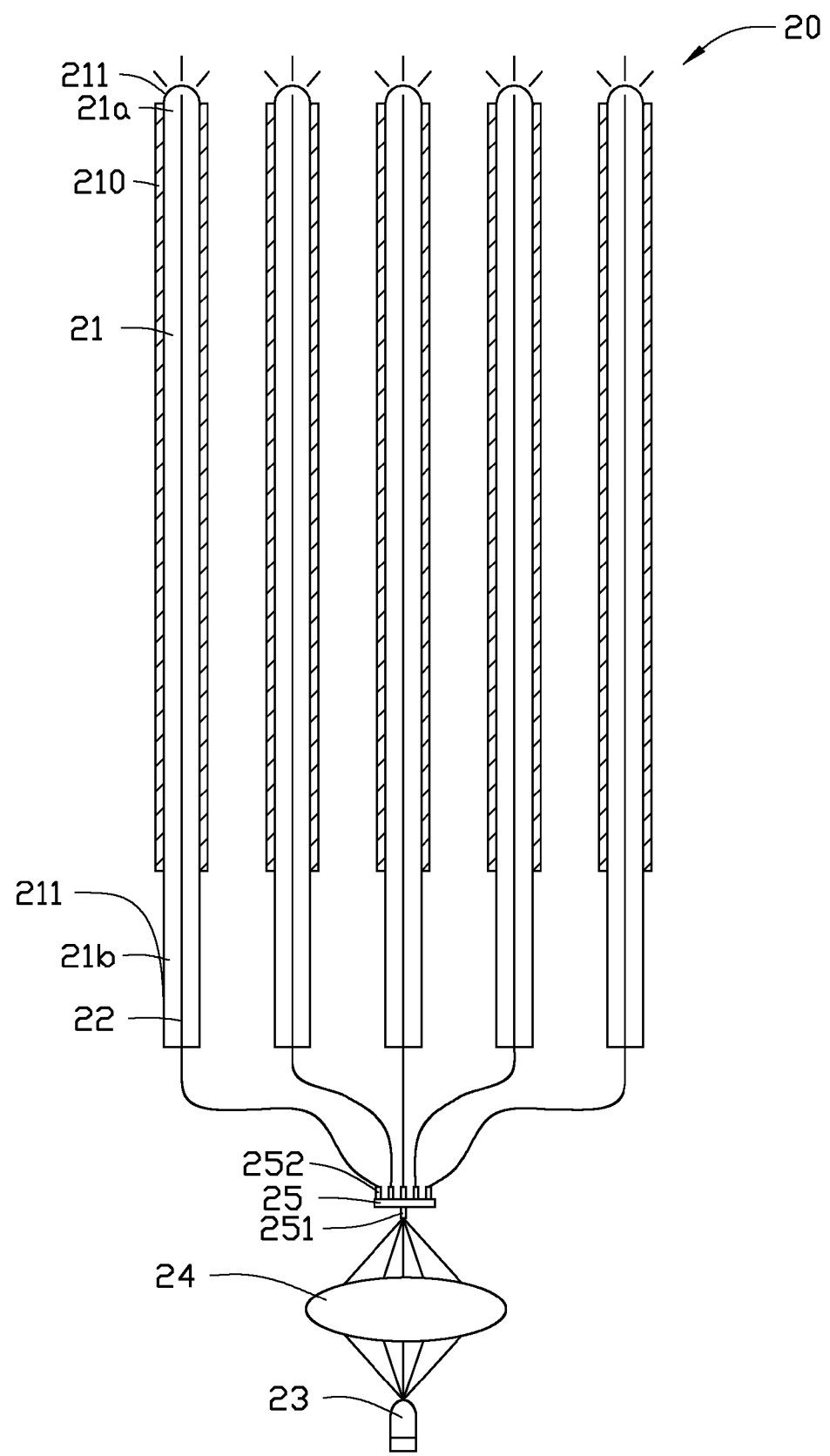

ELECTRONIC INCENSE ASSEMBLY

BACKGROUND

1. Technical Field

The present disclosure relates to electronic incense devices and, particularly, to a low cost electronic incense assembly.

2. Description of Related Art

Electronic incense sticks are typically integrated with electronic burners. In particular, light sources are received in the burner. The electronic incense sticks are stuck in the burner. Each electronic incense stick is a tube having an opaque coating on the outer surface with a transparent bubble on the upper end and guide light emitted from the corresponding light source to the transparent bubble to simulate a burning incense stick. That is, one electronic incense stick requires one corresponding light source, which increases cost.

Therefore, it is desirable to provide an electronic incense assembly, which can overcome the above-mentioned shortcomings.

BRIEF DESCRIPTION OF THE DRAWING

The FIGURE a cross-sectional schematic view of an electronic incense assembly, according to an embodiment.

DETAILED DESCRIPTION

Embodiments of the disclosure will be described in detail, with reference to the accompanying drawing.

Referring to the FIGURE, an electronic incense assembly 20, according to an embodiment, includes a number of electronic incense sticks 21, a number of fibers 22, a light source 23, a converging lens 24, and a fiber optic coupler 25.

The electronic incense sticks 21 are arranged in a bundle configuration or a parallel configuration. Each of the electronic incense sticks 21 includes a transparent tube 211, which has a first end 21a and a second end 21b, and an opaque coating 210 on the outer surface of a major part of the tube 211, adjacent to the first end 21a. The part of the tube 211, which is uncoated, is for simulating the bone of incense sticks. The coated part of the tube 211 and the accompanying opaque coating 210 is for simulating the incense coating of the incense sticks. The first end 21a forms a bubble 211. The second end 21b is opened.

The light source 23 can be a lamp or a light emitting diode and configured for emitting light.

The converging lens 24 is positioned in front of the light source 23 and in the light path of the light source 23 for converging the light emitted from the light source 23.

The fiber optic coupler 25 includes an input 251 for receiving the converged light from the converging lens 24 and a number of outputs 252. The fiber optic coupler 25 is configured for transmitting the converged light from the converging lens 24 to the outputs 252.

The fibers 22 connect to the outputs 252 and extend into the tubes 211 via the second ends 21b to the bubbles 211, respectively.

As such, the light can be transmitted to all the bubbles 211 and all electronic incense sticks 21, sharing the same light source 23, appear burning-like.

Particular embodiments are shown here and described by way of illustration only. The principles and the features of the present disclosure may be employed in various and numerous embodiments thereof without departing from the scope of the disclosure as claimed. The above-described embodiments illustrate the scope of the disclosure but do not restrict the scope of the disclosure.

What is claimed is:

1. An electronic incense assembly, comprising:
a plurality of electronic incense sticks, each of which comprising a transparent tube having a first end and a second end, a bubble forming at the first end, an opaque coating on the outer surface of a part of the tube adjacent to the first end;
a light source for emitting light;
a converging lens for converging the light;
a fiber optic coupler comprising an input for receiving the converged light and a plurality of outputs, the outputs being configured for transmitting the converged light entering the input out of the fiber optic coupler;
a plurality of fibers connecting to the outputs respectively and extending through the tubes to the bubbles respectively.

* * * * *